United States Patent
Koike

(10) Patent No.: US 6,306,414 B1
(45) Date of Patent: Oct. 23, 2001

(54) AQUEOUS SUSPENSION OF AGROCHEMICAL

(75) Inventor: Masahiko Koike, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/341,813

(22) PCT Filed: Feb. 9, 1998

(86) PCT No.: PCT/JP98/00522

§ 371 Date: Jul. 19, 1999

§ 102(e) Date: Jul. 19, 1999

(87) PCT Pub. No.: WO98/34484

PCT Pub. Date: Aug. 13, 1998

(30) Foreign Application Priority Data

Feb. 10, 1997 (JP) .................................................. 9-026953

(51) Int. Cl.$^7$ ...................................................... A01N 25/02
(52) U.S. Cl. ............................................ 424/405; 514/365
(58) Field of Search .............................. 424/405; 514/365

(56) References Cited

U.S. PATENT DOCUMENTS 5,216,009 * 6/1993 Fujimoto et al. .

FOREIGN PATENT DOCUMENTS

| 375907 | 7/1990 | (EP) . |
| 376279 | 7/1990 | (EP) . |
| 418199 | 3/1991 | (EP) . |
| 0425729 | 5/1991 | (EP) . |
| 425978 | 5/1991 | (EP) . |
| 58-124702 | 7/1983 | (JP) . |
| 2-111703 | 4/1990 | (JP) . |
| 4-108704 | 4/1992 | (JP) . |
| 4-112804 | 4/1992 | (JP) . |
| 4-112805 | 4/1992 | (JP) . |
| 4-120007 | 4/1992 | (JP) . |
| 4-334306 | 11/1992 | (JP) . |
| 5-279211 | 10/1993 | (JP) . |

* cited by examiner

Primary Examiner—Diana Dudash
Assistant Examiner—Alysia Berman
(74) Attorney, Agent, or Firm—Wenderoth, Lind & Ponack, L.L.P.

(57) ABSTRACT

The present invention relates to an aqueous suspension comprising (i) a compound of the formula:

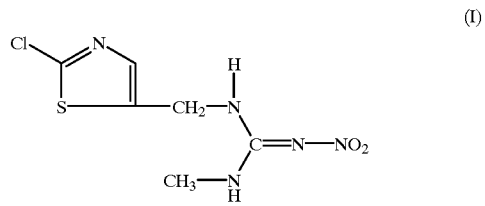

(I)

or a salt thereof, (ii) a condensate of formaldehyde with an aromatic sulfonic acid or a salt thereof or a polyoxyalkylene allyl phenyl ether sulfate, and (iii) an absorptive water-soluble polymer. The aqueous suspension of the invention can be used with advantage as a stable aqueous suspension of low viscosity providing for excellent delivery from a container, with excellent dispersibility in diluent water and excellent long-term fluidity free from caking due to precipitation of the suspended particles.

7 Claims, No Drawings

AQUEOUS SUSPENSION OF AGROCHEMICAL

TECHNICAL FIELD

The present invention relates to an agricultural aqueous suspension characterized by excellent pesticidal activity, low viscosity, and excellent suspension stability.

BACKGROUND ART

Heretofore, as dosage forms for agricultural pesticides, dusts and granules have been primarily used. Those dosage forms are prepared by formulating a small amount of a pesticidally active substance with a large amount of a carrier such as clay, bentonite, calcium carbonate, etc. and, therefore, such formulations must be applied in quantities as large as 2 to 6 kilograms/10 ares in order to insure a uniform distribution of the active substance. This imposes a great burden on the farmers and, moreover, there are many disadvantages in transportation and storage. For this reason, so-called concentrates, which are supplied in small packages to provide for a greater ease of handling, are being developed.

Those concentrates are rich in the active substances and can be applied after dispersion in a suitable diluent, such as water, in the field. Examples include emulsifiable concentrates and wettable powders. However, emulsifiable concentrates require large quantities of an organic solvent for dilution, while it is unavoidable with wettable powders that preparation of sprays in the field involves contaminations with flying solid particles. For those reasons, the recent trend is toward refraining from using those formulations. Wettable granules, which are granular versions of wettable powders have almost overcome the drawbacks of wettable powders but because the size of particles dispersed in water is as large as about 10 and odd μm, application of a dispersion of high concentration causes clogging of the spray nozzle, among other disadvantages.

The compound of the formula (I):

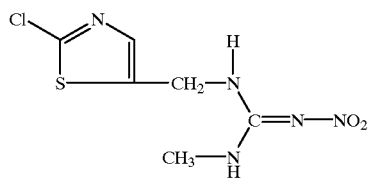

or a salt thereof, is an agricultural pesticide having potent pest-controlling activity.

The demand exists today for development of a stable aqueous suspension of the compound (I) or a salt thereof which should have a low viscosity enough to permit smooth delivery from a container as well as satisfactory dispersibility in diluent water and long-term fluidity free from caking due to precipitation of the suspended particles.

DISCLOSURE OF INVENTION

The inventors of the present invention have made much research to overcome the above-mentioned disadvantages of the prior art and found that an aqueous suspension comprising (i) the compound (I) or a salt thereof, (ii) a condensate of formaldehyde with aromatic sulfonic acid or a salt thereof or a polyoxyalkylene allyl phenyl ether sulfate, and (iii) an absorptive water-soluble polymer in combination may have a low viscosity of not more than 700 mPa·s with excellent dispersibility in diluent water and, in addition, have a long-term stability. The inventors have made further research and have completed the present invention.

Namely, the present invention relates to:

(1) an aqueous suspension which comprises (i) a compound of the formula (I):

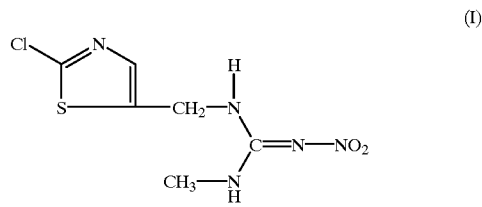

or a salt thereof, (ii) a condensate of formaldehyde with an aromatic sulfonic acid or a salt thereof or a polyoxyalkylene allyl phenyl ether sulfate, and (iii) an absorptive water-soluble polymer, (2) the aqueous suspension as described in (1) above, wherein the aqueous suspension contains about 1 to 10 weight % of the condensate of formaldehyde with aromatic sulfonic acid or a salt thereof or the polyoxyalkylene allyl phenyl ether sulfate in the total aqueous suspension, (3) the aqueous suspension as described in (1) above, wherein the absorptive water-soluble polymer is one or more (preferably one to three) polymers selected from the group consisting of polyvinylpyrrolidone, poly(alkylated vinylpyrrolidone), vinylpyrrolidone-styrene block copolymer and methyl vinyl ether-maleic anhydride copolymer, (4) the aqueous suspension as described in (1) above, which further comprises an unabsorptive water-soluble polymer, (5) the aqueous suspension as described in (4) above, wherein the unabsorptive water-soluble polymer is one or more (preferably one to three) polymers selected from the group consisting of a polymer in the polyol series, a polysaccharides and polyethylene glycol, (6) the aqueous suspension as described in (4) above, wherein the unabsorptive water-soluble polymer is one or more (preferably one to three) polymers selected from the group consisting of xanthan gum, starch and polyethylene glycol, (7) the aqueous suspension as described in (1) above, which further comprises an auxiliary suspending agent, (8) the aqueous suspension as described in (7) above, wherein the auxiliary suspending agent is one or more (preferably one to three) substances selected from the group consisting of montmorillonite, colloidal silicon oxide, silicon oxide-aluminum oxide colloidal mixture and sepiolite, (9) a method for producing the aqueous suspension as described in (1) above, which comprises suspending (i) in the compound of the formula (I):

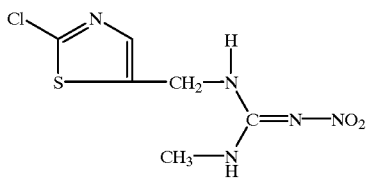

(I)

or a salt thereof, (ii) the condensate of formaldehyde with an aromatic sulfonic acid or a salt thereof or the polyoxyalkylene allyl phenyl ether sulfate, and (iii) the absorptive water-soluble polymer in water, and

(10) a method for controlling a pest which comprises scattering the aqueous suspension as described in (1) above into a field.

BEST MODE FOR CARRYING OUT THE INVENTION

The compound (I) which is guanidine derivative for use in the aqueous suspension of the present invention occurs as trans (E) and cis (Z) isomers in respect of the geometrical orientation of $NO_2$. Preferred, however, is (E)-1-(2-chlorothiazol-5-ylmethyl)-3-methyl-2-nitroguanidine (hereinafter referred to briefly as compound (Ia)).

The salt of compound (I) includes agrochemically acceptable salts with inorganic acids such as hydrochloric acid, hydrobromic acid, hydroiodic acid, phosphoric acid, sulfuric acid, perchloric acid, etc. and salts with organic acids such as formic acid, acetic acid, tartaric acid, malic acid, citric acid, oxalic acid, succinic acid, benzoic acid, picric acid, p-toluenesulfonic acid, etc.

The production method for the compound (I) or a -salt thereof is described in, inter alia, JP-A 157308/1991.

The proportion of compound (I) or a salt thereof in the aqueous suspension of the present invention is generally about 5–60 weight %, preferably about 5–50 weight %, and more preferably about 10–50 weight %, further more preferably 15–45 weight %.

The condensate of formaldehyde with aromatic sulfonic acid or a salt thereof which can be used in preparing the aqueous suspension of the present invention includes a condensate of formaldehyde with a sulfonic acid such as a phenylsulfonic acid, an aryl-substituted phenylsulfonic acid, a phenolsulfonic acid, an aryl-substituted phenolsulfonic acid, p-toluenesulfonic acid, a naphthalene sulfonic acid, an alkyl-substituted naphthalene sulfonic acid, an aralkyl-substituted naphthalene sulfonic acid, an anthracene sulfonic acid, or an alkyl-substituted anthracene sulfonic acid.

The aryl group of the aryl-substituted phenylsulfonic acid or aryl-substituted phenolsulfonic acid as mentioned above includes $C_{6-14}$ aryl groups such as phenyl and naphthyl. The number of the substituents is 1 to 3.

The alkyl group of the alkyl-substituted naphthalene sulfonic acid as mentioned above includes $C_{1-6}$ alkyl groups such as methyl, ethyl, n-propyl, iso-propyl, n-butyl, iso-butyl, sec-butyl and tert-butyl. The number of the substituents is 1 to 7.

The aralkyl group of the aralkyl-substituted naphthalene sulfonic acid as mentioned above includes phenyl-$C_{1-4}$ alkyl groups such as benzyl, phenethyl and phenylpropyl; benzhydryl; and trityl. The number of the substituents is 1 to 3.

The alkyl group of the alkyl-substituted anthracene sulfonic acid as mentioned above includes a $C_{1-6}$ alkyl group such as methyl, ethyl, n-propyl, iso-propyl, n-butyl, iso-butyl, sec-butyl and tert-butyl. The number of the substituents is 1 to 9.

The condensed degree between an aromatic sulfonic acid and formaldehyde is 1.2 to 30, preferably 1.2 to 10.

Among them as mentioned above, a naphthalene sulfonate-formaldehyde condensate is preferable.

The salt of the aromatic sulfonic acid includes alkaline metals such as sodium.

Specific examples of the condensate of formaldehyde with aromatic sulfonic acid or a salt thereof include New Kalgen FS-4 (sodium naphthalenesulfonate-formaldehyde condensate; Takemoto oil & fat co., Ltd.), New Kalgen 9131 (phenylphenolsulfonic acid-formaldehyde condensate; Takemoto oil & fat co., Ltd.), Lavelin FM-L (sodium β-naphthalenesulfonate-formaldehyde condensate; Daiichi Kogyo Seiyaku), New Kalgen WG-2 (sodium β-naphthalenesulfonate-formaldehyde condensate; Takemoto oil & fat co., Ltd.), Demol N (sodium β-naphthalenesulfonate-formaldehyde condensate; Kao Corporation), and Demol C (sodium aromaticsulfonate-formaldehyde condensate; Kao Corporation).

Among them, especially New Kalgen FS-4 is preferable.

The polyoxyalkylene allyl phenyl ether sulfate includes those having a molecular weight of 500–5000.

The polyoxyalkylene in the polyoxyalkylene allyl phenyl ether sulfate includes polyoxyethylene, polyoxypropylene or polyoxybutylene. Especially, New Kalgen FS-7 (Takemoto oil & fat co., Ltd.) which contains mainly polyoxyethylene allyl phenyl ether sulfate is preferable.

The proportion of the condensate of formaldehyde with aromatic sulfonic acid or a salt thereof or the polyoxyalkylene allyl phenyl ether sulfate in the total aqueous suspension of the present invention is generally about 1–10 weight %, preferably about 1–7 weight %.

One or more (preferable one to three) other surfactants such as nonionic or anionic surfactants besides the condensate of formaldehyde with aromatic sulfonic acid or a salt thereof or the polyoxyalkylene allyl phenyl ether sulfate, may be used in combination for preparing the aqueous suspension of the present invention.

The nonionic surfactant include a nonionic surfactant in the ether series such as polyoxyalkylene allyl phenyl ether, polyoxyethylene allyl phenyl ether-formaldehyde condensate, polyoxyethylene alkyl phenyl ethers, polyoxyethylene nonyl phenyl ether, polyoxyethylene distyrenated phenyl ether, polyoxyethylene alkyl allyl ethers, polyoxyethylene alkyl ethers, and polyoxyethylene-polyoxypropylene block copolymer. The nonionic surfactant that can be used in preparing the aqueous suspension of the invention is preferably one having an HLB number in the range of 10–20. The more preferred HLB range is 12–18. Among such surfactants, which are commercially available, are New Kalgen FS-1 (Takemoto oil & fat co., Ltd., polyoxyalkylene allyl phenyl ether), New Kalgen FS-11 (Takemoto oil & fat co., Ltd., polyoxyethylene allyl phenyl ether-formaldehyde condensate), Nonipol 100 (Sanyo Chemical Industries, LTD., polyoxyethylene nonyl phenyl ether), Noigen EA-177 (Daiichi Kogyo Seiyaku, polyoxyethylene distyrenated phenyl ether), Noigen EA-142 (Daiichi Kogyo Seiyaku, polyoxyethylene alkyl allyl ether), and Noigen EA-157 (Daiichi Kogyo Seiyaku, polyoxyethylene alkyl ether).

The anionic surfactant includes metal ligninsulfonates, polyoxyethylene allyl phenyl ether phosphate amine salts, polyoxyethylene alkyl phenyl ether phosphate amine salts, and sodium dialkylsulfo-succinates. To mention commercial products, there can be mentioned New Kalgen WG-4 (Takemoto oil & fat co., Ltd., metal ligninsulfonate), New Kalgen FS-3 (Takemoto oil & fat co., Ltd., polyoxyethylene allyl phenyl ether phosphate amine salt), and New Kalgen FS-31 and FS-32 (Takemoto oil & fat co., Ltd., polyoxyethylene alkyl phenyl ether phosphate amine salt).

The proportion of such a surfactant which may be used in combination in the total aqueous suspension of the present invention is generally about 1–10 weight % and preferably about 1–5 weight %.

To broaden the spectrum of utility of the aqueous suspension of the present invention, the suspension may be supplemented with one or more (preferably one to three) other agrochemicals. As such supplemental agrochemicals, insecticides, bactericides, etc. can be mentioned, which if such are solid at atmospheric temperature. The following are examples of such agrochemicals.

[Insecticides]

Pyridafenthion, dimethoate, PMP, CVMP, dimethylvinphos, acephate, salithion, DEP, NAC, MTMC, MIPC, PHC, MPMC, XMC, bendiocarb, pirimicarb, mesomile, oxamyl, thiodicarb, cypermethrin, caltap hydrochloride, thiocyclam, bensultap, diflubenzuron, teflubenzuron, chlorfluazron, buprofezin, hexythiazox, phenbutatin oxide, pyridaben, clofentezine, nitenpyram, etc.

[Bactericides]

Thiuram, captan, TPN, phthalide, trichlorophos methyl, phosethyl, methyl thiophanate, benomyl, carbendazole, thiabendazole, diethofencarb, iprodione, vinclozolin, procymidone, fluorimide, oxycarboxin, mepronil, flutolanil, bencyclane, metalaxyl, oxadixyl, triadimefon, hexaconazole, trifolin, blasticidin S, kasugamycin, polyoxin, validamycin A, mildeomycin, PCNB, hydroxyisoxazole, dazomet, dimethirimol, diclomezine, triazine, ferimzone, probenazole, isoprothiolane, tricyclazole, pyroquilone, oxolinic acid, etc.

The agrochemicals are not limited to the abovementioned ones but other suitable agrochemicals which are solid at atmospheric temperature can be added.

The absorptive water-soluble polymer is protective colloids which can absorb other hydrophobic substances by a hydrophobic group in the molecular, and which includes a polyvinylpyrrolidone, a poly(alkylated vinylpyrrolidone), a vinylpyrrolidone-styrene block copolymer and a methylvinyl ether-maleic anhydride copolymer.

The polyvinylpyrrolidone includes those having a mean molecular weight of 5,000–2,000,000 such as Agrimer 15 (mean molecular weight: about 8000), Agrimer 30 (mean molecular weight: about 57500), Agrimer 60 (mean molecular weight: about 406000) and Agrimer 90 (mean molecular weight: about 1270000), any of which are manufactured by ISP Ltd.

The alkyl of poly(alkylated vinylpyrrolidone) includes $C_{1-30}$ alkyl groups such as methyl, ethyl, n-propyl, isopropyl, n-butyl, iso-butyl, sec-butyl, tert-butyl, pentyl, isopentyl, tert-pentyl, neopentyl, hexyl, isohexyl, 2,2-dimethylbutyl, heptyl, 2-methylhexyl, octyl, 2,2,4-trimethylpentyl, nonyl, decyl, undecyl, dodecyl, tridecyl, tetradecyl, pentadecyl, hexadecyl, heptadecyl, octadecyl, nonadecyl, icosyl, henicosyl, dococyl, tricosyl and tetracosyl. Among them, $C_{1-24}$ alkyl groups are preferable. Especially, $C_4$, $C_{16}$ and $C_{20}$ alkyl groups are preferable. Moreover, degree of alkylation of the poly (alkylated vinylpyrrolidone) is preferably 5–90%, more preferably 5–15% and 40–60%. The mean molecular weight of the poly(alkylated vinylpyrrolidone) is preferably about 1,000 to about 100,000. Examples of the poly(alkylated vinylpyrrolidone) include Agrimer AL-10 (number of carbon atom in the alkyl group: 4, degree of alkylation: about 10%, mean molecular weight: about 70000), Agrimer AL-10LC (number of carbon atom in the alkyl group: 4, degree of alkylation: about 10%, mean molecular weight: about 70000), Agrimer AL-25 (number of carbon atom in the alkyl group: 16, degree of alkylation: about 50%, mean molecular weight: about 9500), and Agrimer AL-904 (number of carbon atom in the alkyl group: 4, degree of alkylation: about 10%, mean molecular weight: about 16,000), any of which are manufactured by ISP Ltd.

The vinylpyrrolidone-styrene block copolymer includes those having a mean molecular weight of about 40000 such as Agrimer ST (ISP Ltd.).

The methylvinylether-maleic anhydride copolymer includes free acid from having a mean molecular weight of about 100,000 to 300,000 such as Agrimer VEMA H-240 (ISP Ltd.), anhydride form having a mean molecular weight of about 100,000 to about 300,000 such as Agrimer VEMA AN216 (ISP Ltd.), or half esters form having a mean molecular weight of about 20,000 to about 60,000 such as Agrimer ES-22 (ISP Ltd.).

As other absorptive water-soluble polymer which may be used in combination for preparing the aqueous suspension, poly(sodium acrylate) and carboxymethylcellulose are also mentioned.

As the absorptive water-soluble polymer, poly(alkylated vinylpyrrolidone) is preferable.

The proportion of the absorptive water-soluble polymer in the total aqueous suspension of the present invention is generally about 0.05–5 weight %, preferably about 0.1–3 weight %, more preferably about 0.1–2 weight %.

For the purpose of stabilizing and adjusting the viscosity of the suspension, the aqueous suspension of the present invention may be further supplemented with an unabsorptive water-soluble polymer and/or an auxiliary suspending agent.

The unabsorptive water-soluble polymer includes polymers in the polyol series (e.g. Agrisol FL-104FA, Kao Corporation); polysaccharides such as gum arabic, gelatin, guar gum, xanthan gum (e.g. Rhodopol 23; Rhone-Poulenc), starch (e.g. Stabirose MKK 100; Matsutani Chemical Industry co., LTD.), starch derivatives such as hydrolyzed starch (e.g. Pine-Dex; Matsutani Chemical Industry co., LTD.), soluble-starch (e.g. Stabirose S-10; Matsutani Chemical Industry co., LTD.), enzymatically denatured starch (e.g. Amicol 6L; Nippon Starch Refining co., LTD.) and pregelatinized starch (e.g. Cornalpha; Nippon Starch Refining co., LTD.) and dextrins (e.g. dextrin, cyclodextriri); and polyethylene glycol (e.g. PEG 6000; Sanyo Chemical Industries, LTD.).

Among them, the polysaccharides such as xanthan gum and starch, and polyethylene glycol are preferable.

When the unabsorptive water-soluble polymer is used, it is used in a proportion of generally about 0.05–10 weight %, preferably about 0.05–3 weight % based on the total suspension.

The auxiliary suspending agent is water-insoluble additive and includes montmorillonite (e.g. Kunipia F; Kunimine Industries co., LTD., Laponite; Nisshin Chemical Industries, LTD.), colloidal silicon oxide (e.g. Aerosil series such as Aerosil 200; Aerosil NIPPON), silicon oxide-aluminum oxide colloidal mixture (e.g. Aerosil COK84: $SiO_2/Al_2O3$ =82 to 86 (%)/14 to 18 (%); Aerosil NIPPON) and sepiolite (e.g. Aidplus ML70DS-NV; Mizusawa Industrial Chemicals Ltd.).

Among them, montmorillonite is preferable.

When the auxiliary suspending agent is used, it is used in proportion of generally about 0.05–10 weight %, preferably about 0.1–3 weight % based on the total suspension.

Those additives such as unabsorptive water-soluble polymers and auxiliary suspending agent can be used each alone or in combination.

In addition, other additives for routine use in aqueous suspensions in general can also be incorporated in the aqueous suspension of the present invention. For example, a pH control agent, an antifreeze agent, an antifoam agent, and/or an antiseptic agent can be added liberally but selectively according to the amount of the agrochemical used. The pH control agent may for example be citric acid monohydrate. The antifreeze agent that can be used includes, but is not limited to, ethylene glycol, diethylene glycol, and glycerin. The antifoam agent may for example be a silicone series defoaming agent (e.g. Anti-foam E-20; KAO Corporation). The antiseptic agent includes, but is not limited to, n-butyl p-hydroxybenzoate, potassium sorbate, and sorbic acid.

The pH control agent, when used, is added in a proportion of generally about 0.01–5 weight % or preferably about 0.05–3 weight % based on the total suspension. The antifreeze agent, when used, is used in a proportion of generally about 1–20 weight % or preferably about 3–10 weight % based on the total suspension. The antifoam agent, when used, is added in a proportion of generally about 0.05–0.5 weight % or preferably about 0.05–0.3 weight % based on the total suspension. The antiseptic agent, when used, is added in an amount of generally about 0.01–3 weight % or preferably about 0.01–1.5 weight % of the total suspension.

The aqueous suspension of the present invention can be produced by suspending (i) the compound (I) or a salt thereof, (ii) a condensate of formaldehyde with aromatic sulfonic acid or a salt thereof or a polyoxyalkylene allyl phenyl ether sulfate, and (iii) an absorptive water-soluble polymer in water in accordance with the per se known method or any other technique analogous thereto. For example, there can be mentioned a process (1) which comprises mixing all the components together thoroughly in a high-speed mixer for about 20–60 minutes and pulverizing and dispersing the mixture by means of a wet mill such as Dynomill or a microfluidizer and a process (2) which comprises grinding bulk powders of the active substance, e.g. compound (I) or a salt thereof, in a dry mill such as Jetmizer and blending and dispersing the finely divided powders with the other components in a high-speed mixer for about 30–90 minutes.

As it may be understood from the above description of the production method, the effective ingredient for the aqueous suspension of the present invention is dispersed in finely divided form in water. In the presence of other powder components, too, the effective ingredient is dispersed as efficiently in water. The mean diameter of the dispersed particles is not greater than about 10 $\mu$m, preferably 0.1–5 $\mu$m.

The crop plant to which the aqueous suspension of the present invention can be applied includes rice, wheat, barley, sugar beet, maize (Indian corn), cotton, vegetables (e.g. cabbage, Chinese cabbage, radish, cucumber, eggplant, potato, etc.), fruit-bearing trees (e.g. mandarin orange, peach, pear, etc.), tea, and tobacco.

The pest which can be controlled with the aqueous suspension of the present invention includes insects of the order Hemiptera {e.g. cabbage stink bug [*Eurydema ruaosum* Motschulsky], black rice stink bug [*Scotinophara lurida* Burmeister], bean bug [*Riptortus clavatus* Thunberg], pear lace-bug [*Stephanitis nashi* Esaki et Takeya], brown planthopper [*Nilaparvata lugens* Stal], white-back planthopper [*Sogota furcifera* Horvath], smaller brown planthopper [*Delphacodes striatella* Fallén], green rice leafhopper [*Nephotettix bipuntatus cincticeps* Uhler], tea green leafhopper [*Chlorita onukii* Matsuda], greenhouse whitefly [*Trialeurodes vaporariorum*], arrow-head scale [*Prontaspis yanonensis* Kuwana], mulberry mealy bug [*Pseudococcus comstocki* Kuwana], soybean aphid [*Aphis glycines* Matsumura], turnip aphid [*Rhopalosiphum pseudobrassicae* Davis], cabbage aphid [*Brevicoryne brassicae* Linné], greenhouse aphid [*Myzus persicae* Sulzer], cotton aphid [*Aphis gossypii* Glover], apple aphid [*Aphis pomi* DeGeer], etc.}, the order Lepidoptera {e.g. tabacco cutworm [*Prodenia litura* Fabricius], diamond-back moth [*Plutella maculipennis* Curtis], cabbage butterfly [*Pieris rapae* Linné], Asiatic rice borer [*Chilo suppressalis* Walker], beet worm [*Plusia nigrisigna* Walker], oriental tobacco budworm [*Helicoverpa assulta assulta* Guenée], armyworm [*Leucania separata* Walker], cabbage armyworm [*Mamestra brassicae* Linné], smaller tea tortrix [*Adoxophyes orana* Fischer von Röslerstamm] (apple), cotton leaf roller [*Sylepta derogata* Fabricius], grass leaf roller [*Cnaphalocrocic medinalis* Guénée], potato tuberworm [*Phthorimaea operculella* Zeller], tea leaf roller [*Caloptilia theivora* Walsingham], smaller tea tortrix [*Adoxophyes orana* Fischer von Röslerstamm] (tea), etc.}, the order Coleoptera {e.g. potato lady beetle [*Evilachna sparsa* orientalis Dieke], cucurbit leaf beetle [*Rhaphidopalpa femoralis* Motschulsky], striped cabbage flea-beetle [*Phyllotreta vittata* Fabricius], Colorado potato bug [*Leptinotarsa decemlineata*], beet tortoise beetle [*Cassida nebulosa* Linne], rice leaf beetle [*Oulema oryzae* Kuwayama], rice plant weevil [*Echinocnemus sauameus* Billberg], vegetable weevil [*Listroderes obliquus* Klug], etc.}, the order Diptera {e.g. oriental house fly [*Musca domestica vicina* Macquart], pale house mosquito [*Culex pipiens pallens* Coquillett], common horse fly [*Tabanus trigonus* Coquillett], onion maggot [*Hylemya antiqua* Meigen], seed-corn maggot [*Hylemya platura* Meigen], etc.}, the order Orthoptera {e.g. Asiatic locust [*Locusta migratoria* Linne], African mole cricket [*Gryllotalpa africana* Palisot de Beauvois], etc.}, reticulopterous insects {e.g. German cockroach [*Blattella germanica* Linne], smoky-brown cockroach [*Periplaneta fuliginosa* Serville], etc.}, spider mites {e.g. two-spotted spider mite [*Tetranychus urticae* Koch], citrus red mite [*Panonychus citri* McGregor], Kanzawa spider mite [*Tetranychus kanzawai* Kishida], carmine mite [*Tetranychus telarius* Linne], European red mite [*Panonychus ulmi* Koch], Japanese citrus rust mite [*Aculus pelekassi* Keifer], etc.}, nematodes {e.g. rice white-tip nematode [*Aphelenchoides besseyi* Christie] etc.} and so on.

The aqueous suspension of the present invention is a safe and useful agrochemical composition with low toxicity against plants and mammals. This agrochemical composition can be used either as it is or as dilution in a suitable medium, e.g. water, when used. The recommended method for application depends on the crop plant applied, but is generally scattering by means of spraying or dropping, or dipping to field, i.e. paddy field, plow-land, orchard, grass-land or non-crop land in accordance with the per se known method. The specific method for application includes aerial broadcast, soil treatment, folial application, nursery box treatment, hand applica tion along rows, seed dressing, bed soil treatment, directed application to infesting pests, application to paddy flood water, etc.

The recommended dose of the aqueous suspension of the present invention depends on the concentration of the agrochemical active ingredient but is generally about 1–500 g, preferably about 1–200 g, as active ingredient, per 10 ares for paddy field and plow-land (growing tea, wheat, sugar beet, maize, potato, cotton, etc.) pests and orchard pests.

EXAMPLES

The following examples and test examples are intended to illustrate the present invention in further detail. The compound (Ia) used here was prepared in accordance with the procedure described in JP-A 15 7308/1991 (Table 4; Compound No. 19). It should be understood that all parts and percents (%) are by weight unless otherwise indicated.

Example 1

| | |
|---|---|
| Compound (Ia) | 20 parts |
| New Kalgen FS-4 | 5 parts |
| Agrimer 30 | 1 part |
| Polyethylene glycol (PEG6000) | 2 parts |
| Rhodopol 23 | 0.1 part |
| Anti-foam E-20 | 0.2 part |
| Ethylene glycol | 4 parts |
| Kunipia F | 1 part |
| n-Butyl p-hydroxybenzoate | 0.1 part |
| Water | add 100 parts |

The above components were thoroughly mixed in a high-speed mixer and wet-pulverized (one pass) by means of Dynomill (Shinmaru Enterprises, 1.0 mm glass beads, packing rate 80%, peripheral speed 15 m/s) to provide an aqueous suspension containing 20% of compound (Ia).

The term of "add 100 parts" means to make 100 parts of aqueous suspension by adding water besides other components.

Example 2

| | |
|---|---|
| Compound (Ia) | 20 parts |
| New Kalgen FS-4 | 2 parts |
| Agrimer AL-10 | 1 part |
| Stavirose MKK 100 | 0.5 part |
| Anti-foam E-20 | 0.2 part |
| Ethylene glycol | 4 parts |
| Aerosil COK84 | 1 part |
| n-Butyl p-hydroxybenzoate | 0.1 part |
| Water | add 100 parts |

Using the above components, the procedure of Example 1 was repeated to provide an aqueous suspension containing 20% of compound (Ia).

Example 3

| | |
|---|---|
| Compound (Ia) | 20 parts |
| New Kalgen FS-7 | 3 parts |
| Agrimer ST | 1 part |
| Anti-foam E-20 | 0.2 part |
| Ethylene glycol | 4 parts |
| Aidplus ML70DS-NV | 1 part |
| n-Butyl p-hydroxybenzoate | 0.1 part |
| Water | add 100 parts |

Using the above components, the procedure of Example 1 was repeated to provide an aqueous suspension containing 20% of compound (Ia).

Example 4

| | |
|---|---|
| Compound (Ia) | 20 parts |
| New Kalgen FS-7 | 3 parts |
| Agrimer VEMA H-240 | 0.5 part |
| Anti-foam E-20 | 0.2 part |
| Ethylene glycol | 4 parts |
| Kunipia F | 1.5 part |
| Citric acid monohydrate | 0.1 part |
| n-Butyl p-hydroxybenzoate | 0.1 part |
| Water | add 100 parts |

Using the above components, the procedure of Example 1 was repeated to provide an aqueous suspension containing 20% of compound (Ia).

Example 5

| | |
|---|---|
| Compound (Ia) | 40 parts |
| New Kalgen FS-7 | 5 parts |
| Agrimer AL-30 | 1 part |
| Anti-foam E-20 | 0.2 part |
| Ethylene glycol | 7 parts |
| Aerosil COK84 | 1.5 part |
| Rhodopol 23 | 0.2 part |
| n-Butyl p-Hydroxybenzoate | 0.1 part |
| Water | add 100 parts |

Using the above components, the procedure of Example 1 was repeated to provide an aqueous suspension containing 40% of compound (Ia).

Example 6

| | |
|---|---|
| Compound (Ia) | 21 parts |
| New Kalgen FS-4 | 2 parts |
| Agrimer AL-10 | 0.5 part |
| Stabirose MKK 100 | 0.3 part |
| Rhodopol 23 | 0.1 part |
| Kunipia F | 0.8 part |
| n-Butyl p-hydroxybenzoate | 0.1 part |
| Anti-foam E-20 | 0.2 part |
| Ethylene glycol | 4 parts |
| Water | add 100 parts |

Using the above components, the procedure of Example 1 was repeated to provide an aqueous suspension containing 21% of compound (Ia).

Example 7

| Compound (Ia) | 21 parts |
|---|---|
| New Kalgen FS-4 | 2 parts |
| Agrimer AL-10 | 0.5 part |
| Polyethylene glycol (PEG6000) | 2.0 part |
| Rhodopol 23 | 0.05 part |
| Kunipia F | 0.65 part |
| n-Butyl p-hydroxybenzoate | 0.1 part |
| Anti-foam E-20 | 0.2 part |
| Ethylene glycol | 4 parts |
| Water | add 100 parts |

Using the above components, the procedure of Example 1 was repeated to provide an aqueous suspension containing 21% of compound (Ia).

Example 8

| Compound (Ia) | 21 parts |
|---|---|
| New Kalgen FS-4 | 2 parts |
| Agrimer AL-10 | 0.5 part |
| Polyethylene glycol (PEG6000) | 2 parts |
| Kunipia F | 0.8 part |
| n-Butyl p-hydroxybenzoate | 0.1 part |
| Anti-foam E-20 | 0.2 part |
| Ethylene glycol | 4 parts |
| Water | add 100 parts |

Using the above components, the procedure of Example 1 was repeated to provide an aqueous suspension containing 21% of compound (Ia).

Test Example 1

Using the aqueous suspensions prepared in Examples 1–8, the viscosity, water dispersibility, stability of 10-fold diluted suspension and tendency toward caking of each aqueous suspension were evaluated by the following methods.

(1) Viscosity

Viscosity was measured with a Type B viscosimeter at 25° C.

(2) Water Dispersibility

A hollow cylinder of 500 ml capacity was filled in with 500 ml of water. Then, 0.5 ml of the test suspension was added dropwise and the dispersion was evaluated according to the criteria: (A) excellent, (B) good, (C) poor, and (D) not dispersed.

(3) Stability Test of 10-fold Diluted Suspension

A hollow cylinder of 500 ml capacity was filled in with 450 ml of water and 50 ml of diluted suspension (flowable), and then turned upside down 10 times.

The test suspensions were respectively allowed to stand for 15 hours and the degree of the separation of water-phase was investigated.

(4) Tendency Toward Caking

The test suspensions were respectively allowed to stand at room temperature for 12 months following preparation and the degree of caking on the container bottom was investigated.

The results are shown in Table 1.

TABLE 1

| Sample | Viscosity (mPa · s) | Water dispersibility | Degree of separation (%) | Caking |
|---|---|---|---|---|
| Ex. 1 | 230 | A | 2.1 | non |
| Ex. 2 | 150 | A | 1.8 | non |
| Ex. 3 | 65 | A | 3.2 | non |
| Ex. 4 | 370 | A | 3.0 | non |
| Ex. 5 | 280 | A | 1.1 | non |
| Ex. 6 | 290 | A | 2.1 | non |
| Ex. 7 | 390 | A | 2.4 | non |
| Ex. 8 | 250 | A | 2.1 | non |

It is clear from Table 1 that the aqueous suspension of the present invention is of low viscosity, i.e. not higher than 700 mPa·s, with good water dispersibility and has a good shelf-life (stability of the stock suspension).

Industrial Applicability

The aqueous suspension comprising (i) the compound (I) or a salt thereof, (ii) the condensate of formaldehyde with aromatic sulfonic acid or a salt thereof or the polyoxyalkylene allyl phenyl ether sulfate, and (iii) an absorptive water-soluble polymer can be used with advantage as a highly stable agrochemical preparation with a low viscosity, i.e. not higher than 700 mPa·s, thus providing for excellent delivery from a container with excellent dispersibility in diluent water and excellent long-term fluidity free from caking due to precipitation of the suspended particles.

What is claimed is:

1. An aqueous suspension which comprises (i) a compound of the formula (I):

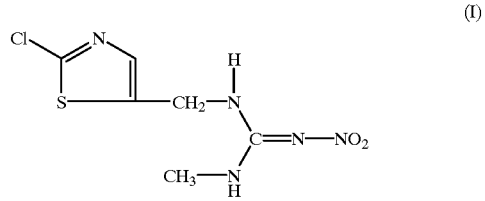

or a salt thereof, (ii) a naphthalene sulfonate-formaldehyde condensate, and (iii) one or more absorptive water-soluble polymers selected from the group consisting of polyvinylpyrrolidone, poly(alkylated vinylpyrrolidone), vinylpyrrolidone-styrene block copolymer and methyl vinyl ether-maleic anhydride copolymer.

2. The aqueous suspension as claimed in claim 1 wherein the aqueous suspension contains about 1 to 10 weight % of the naphthalene sulfonate-formaldehyde condensate in the total aqueous suspension.

3. The aqueous suspension as claimed in claim 1 which further comprises one or more unabsorptive water-soluble polymers selected from the group consisting of xanthan gum, starch and polyethylene glycol.

4. The aqueous suspension as claimed in claim 1 which further comprises an auxiliary suspending agent.

5. The aqueous suspension as claimed in claim 4 wherein the auxiliary suspending agent is one or more substances selected from the group consisting of montmorillonite, colloidal silicon oxide, silicon oxide-aluminum oxide colloidal mixture and sepiolite.

6. A method for producing the aqueous suspension as claimed in claim 1 which comprises suspending (i) a compound of the formula (I):

$$\text{Cl} - \underset{S}{\underset{|}{\bigcirc}} \overset{N}{=} - CH_2 - \overset{H}{\underset{|}{N}} - \underset{\underset{H}{\overset{|}{N}} - CH_3}{\overset{}{C}} = N - NO_2 \quad (I)$$

or a salt thereof, (ii) a naphthalene sulfonate-formaldehyde condensate, and (iii) one or more absorptive water-soluble polymers selected from the group consisting of polyvinylpyrrolidone, poly(alkylated vinylpyrrolidone), vinylpyrrolidone-styrene block copolymer and methyl vinyl ether-maleic anhydride copolymer in water.

7. A method for controlling a pest which comprises scattering the aqueous suspension as claimed in claim 1 into a field.

* * * * *